United States Patent [19]

Seidel et al.

[11] Patent Number: 4,816,461

[45] Date of Patent: Mar. 28, 1989

[54] 7,8,9,10-TETRAHYDROTHIENO[3,2-E]PYRIDO[4,3-B] INDOLE, A PROCESS FOR THEIR PREPARATION AND MEDICAMENTS CONTAINING THEM

[75] Inventors: Peter-Rudolf Seidel, Cologne; Günter Schöllnhammer, Bergisch-Gladbach, both of Fed. Rep. of Germany

[73] Assignee: Troponwerke GmbH & Co. KG, Cologne, Fed. Rep. of Germany

[21] Appl. No.: 61,255

[22] Filed: Jun. 10, 1987

Related U.S. Application Data

[63] Continuation of Ser. No. 846,333, Mar. 28, 1986, which is a continuation of Ser. No. 587,081, Mar. 7, 1984, abandoned.

[30] Foreign Application Priority Data

Mar. 29, 1983 [DE] Fed. Rep. of Germany ....... 3311342

[51] Int. Cl.$^4$ .................... A61K 31/44; C07D 495/14
[52] U.S. Cl. ...................................... 514/287; 546/64; 549/42
[58] Field of Search ........................... 546/64; 514/287

[56] References Cited

U.S. PATENT DOCUMENTS 4,410,536  10/1983  Boltze et al. .......................... 546/64

FOREIGN PATENT DOCUMENTS 3311342  10/1984  Fed. Rep. of Germany .

Primary Examiner—Donald G. Daus
Assistant Examiner—William A. Teoli, Jr.
Attorney, Agent, or Firm—Sprung Horn Kramer & Woods

[57] ABSTRACT

The invention concerns the provision of 7,8,9,10-tetrahydrothieno[3,2-e]pyrido[4,3-b] indoles, useful, inter alia, as antidepressants, and intermediates for the preparation thereof. Also included in the invention are compositions containing said indoles and methods for the use of said indoles and indole compositions as antidepressants.

15 Claims, No Drawings

7,8,9,10-TETRAHYDROTHIENO[3,2-E]PYRIDO[4,3-B] INDOLE, A PROCESS FOR THEIR PREPARATION AND MEDICAMENTS CONTAINING THEM

This is a continuation of application Ser. No. 846,333, filed Mar. 28, 1986 now pending, which is a continuation of Ser. No. 587,081, filed Mar. 7, 1984 now abandoned.

The present invention relates to new substituted 7,8,9,10-tetrahydrothieno[3,2-e]pyrido[4,3-b]indoles, a process for their preparation and medicaments containing them, and their use as medicaments, in particular as agents which influence the central nervous system.

Some 7,8,9,10-tetrahydrothieno[3,2-e]pyrido[4,3-b]indoles and their actions on the central nervous system, in particular their antidepressant actions, have already been described generally in European Patent Specification No. 12,347. However, the action of these compounds is not always completely satisfactory.

It has now been found that the new substituted 7,8,9,10-tetrahydrothieno[3,2-e]pyrido[4,3-b]indoles of the formula I

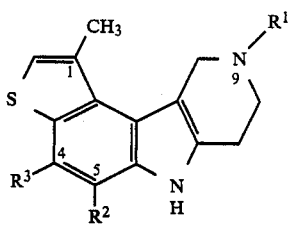

in which
$R^1$ represents hydrogen or alkyl and
$R^2$ and $R^3$ represent a hydrogen atom and a halogen atom or two identical or different halogen atoms,
and acid addition salts thereof, have good properties in respect of the central nervous system, in particular good antidepressant properties.

Surprisingly, the new substituted 7,8,9,10-tetrahydrothieno[3,2-e]pyrido[4,3-b]indole derivatives of the formula (I) to be used according to the invention have a better spectrum of action on the central nervous system, in particular a better therapeutically useful in vivo activity, than the compounds known from the prior art and described in European Patent Specification No. 12,347. The compounds of the formula (I) according to the invention and their pharmaceutical use thus represent an enrichment of pharmacy.

Formula (1) provides a definition of the substituted 7,8,9,10-tetrahydrothieno[3,2-e]pyrido[4,3-b]indole derivatives according to the invention. Preferred compounds of the formula (I) are those in which
$R^1$ represents hydrogen or straight-chain or branched $C_1$-$C_4$-alkyl and
$R^2$ and $R^3$, as halogen, represent fluorine or chlorine.

The present invention furthermore relates to a process for the preparation of compounds of the formula (I), characterised in that hydrazine compounds of the formula (II)

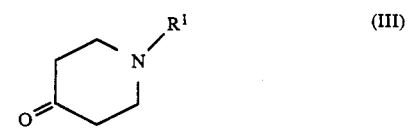

in which $R^2$ and $R^3$ have the meaning given above, are reacted with piperidones of the formula (III)

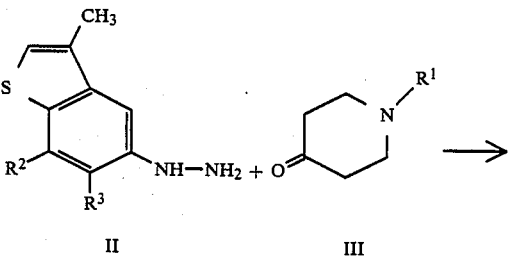

in which $R^1$ has the meaning given above, or with salts (especially acid-addition salts) of these piperidones, using inorganic or organic solvents at temperatures between 20° and 250° C., if appropriate in the presence of condensing agents, and, if appropriate, the compounds of the formula (I) thus obtained are then converted into the acid addition salts in a known manner.

The new compounds of the formula (I) have surprisingly pronounced and advantageous actions on the central nervous system. Their use as antidepressants is mentioned in particular.

The advantage of these new compounds is that they can no longer be metabolised by hydroxylation at the substitution points labelled $R^2$ and $R^3$, where $R^2$ and $R^3$ have the meaning given above.

Compounds of the formula (I) which are of particular importance and are particularly preferred according to the invention are those in which
$R^1$ represents hydrogen, methyl, ethyl, propyl, i-propyl, n-butyl, i-butyl or t-butyl and
$R^2$ and $R^3$, as halogen, represent fluorine.

Very particularly preferred compounds of the general formula (I) are those in which
$R^1$ represents methyl or ethyl,
$R^2$ represents fluorine and
$R^3$ represents hydrogen.

The starting compounds of the formula (II) required for the preparation of compounds of the formula (I) and their preparation are likewise an essential component of this invention.

The preparation of the compounds of the formula (I) according to the invention from hydrazine compounds of the formula (II) and piperidones of the formula (III) according to the following equation:

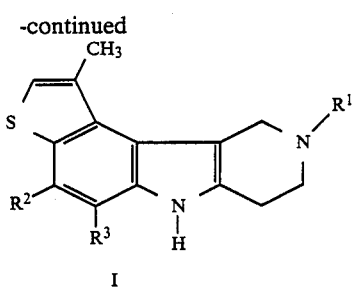

can be carried out by two different variants, depending on the reactivity of the reactants:

Variant (a): In the case of the acid-insensitive reactants (II and III), salts thereof, preferably the hydrochlorides, are used, in a suitable diluent.

Variant (b): In the case of reactants (II and III) which are preferably reacted in the form of their bases to give compounds of the formula (I) or are distinguished by sensitivity towards acids, the reaction is preferably carried out at elevated temperatures in the presence of high-boiling solvents or without a solvent.

In both reaction variants, it is advantageous to carry out the reactions under an inert gas atmosphere, such as, for example, nitrogen or argon.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Suitable solvents which are suitable for process variant (a) are all the solvents customary for the Fischer indole synthesis (compare E. Enders, Houben-Weyl, Volume 10/2, pages 546–586, 1967; and A. Weissberger, The Chemistry of Heterocyclic Compounds, Indole, Part I, pages 232–370, 1972).

Examples which may be mentioned are: water, methanol, ethanol, propyl alcohol, isopropyl alcohol, benzene, toluene, xylene, dioxane, glacial acetic acid, propionic acid, ethyl polyphosphate and high-boiling hydrocarbons.

The condensing agents used are likewise the catalysts customary for indole ring closure.

Examples which may be mentioned are: zinc chloride, boron trifluoride, boron trifluoride etherate, hydrogen chloride, hydrochloric acid, sulphuric acid, phosphoric acid, polyphosphoric acid, ethyl polyphosphate, formic acid, trifluoroacetic acid, acid ion exchangers, such as, for example Amberlite, and a mixture of glacial acetic acid/hydrogen chloride.

The reaction temperatures can be varied within a substantial range. In general, the reaction is carried out between 40° C. and 150° C., preferably between 60° C. and 120° C. The reaction times vary between 0.5 and 20 hours, depending on the reaction temperature.

The reaction is usually carried out under atmospheric pressure.

In carrying out process (a) according to the invention, the piperidone (III) is advantageously used in an excess of 0.1 to 0.5 mole per mole of the hydrazine compound (II).

The reaction can advantageously also be carried out under an inert gas, such as, for example, nitrogen or argon. In individual cases, the ketone of the formula (III) can also advantageously be used as the corresponding ketal, such as, for example, ethylene ketal or propylene ketal.

The reaction products are advantageously worked up by evaporating the reaction solution, taking up the concentrate in a suitable inert organic solvent, rendering the mixture alkaline with a base, for example NaOH or $NH_3$, and purifying the product, if necessary with the aid of chromatography on silica gel or aluminium oxide or other suitable adsorbents.

Process variant (b) is preferably carried out at temperatures between 150° and 210° C. An inert gas atmosphere is advantageously used. Examples which may be mentioned of solvents for this reaction variant are: tetralin, dichlorobenzene, acetamide, ethylene glycol, diethylene glycol, diethylene glycol monomethyl ether, triethylene glycol, glycerol, N-methyl-pyrrolidone, ethylene glycol dimethyl ether and diethylene glycol dibutyl ether, ethylene glycol being mentioned as particularly preferred.

Compounds of the formula (I) in which the substituent $R^1$ on the nitrogen represents hydrogen can subsequently be converted into correspondingly substituted compounds by known methods. A subsequent substitution of this type is preferably carried out by reaction with the correspondingly substituted halides, such as, for example, alkyl halides, preferably methyl iodide, ethyl bromide, ethyl iodide, propyl bromide, isopropyl chloride and n-butyl bromide, in particular methyl iodide, ethyl bromide or ethyl iodide, or with the correspondingly substituted acid halides, such as, for example, acetyl bromide or acetyl chloride, in a manner which is known per se, and subsequent reduction with complex metal hydrides, preferably with lithium aluminium hydride, in a manner which is known per se.

If the basicity of the NH group in the tetrahydropyridine part of I where $R^1$ represents H is sufficient, the acylation and alkylation can also be carried out, where relevant, directly in the presence of suitable proton acceptors, such as trimethylamine, triethylamine, N-methylmorpholine, N-methylpiperidine, N,N-dimethylaniline, N,N-diethylaniline or heterocyclic bases, such as pyridine, picolines, collidines, quinoline or isoquinoline.

The reaction can be carried out without a solvent or in the presence of suitable solubilising agents. Possible solubilising agents are all the organic solvents which are inert towards the particular reactants. These include, preferably, aromatic hydrocarbons, such as benzene, toluene, xylene or tetralin; ethers, such as diethyl ether, diisopropyl ether, tetrahydrofuran, dioxane and ethylene glycol diethyl ether; nitriles, such as acetonitrile and propionitrile; carboxylic acid amides, such as dimethylformamide and dimethylacetamide, hexamethylphosphoric acid triamide; N-methylpyrrolidone; dimethylsulphoxide; heterocyclic bases, such as pyridine, quinoline or picolines, and also commercially available technical grade mixtures of these solvents.

The reaction can be carried out under normal pressure or under increased pressure; increased pressure may be necessary for the reaction, especially if low-boiling alkyl halides are used as reactants.

The reaction temperatures can be varied within a certain range. In general, the reaction is carried out at temperatures between 0° and 200° C., preferably between 20° and 150° C., and in particular between 40° and 80° C.; room temperature is sufficient in individual cases.

Working up can then be carried out in a manner analogous to that described under process variant (a).

The 3-methyl-5-hydrazinobenzothiophenes of the formula (II) to be used as precursors, in which

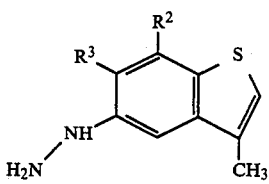
(II)

$R^2$ and $R^3$ preferably, as halogen, represent fluorine and/or chlorine, are new and are likewise the subjects of the present invention. They can be prepared in a generally customary and known manner, by a process in which the 3-methyl-5-nitrobenzothiophenes, which are new and are likewise a component of the invention, of the formula (IV)

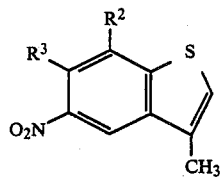
(IV)

in which $R^2$ and $R^3$ have the meaning given in the case of the general formula (I), are reduced with reducing agents to give the new 5-amino-3-methylbenzothiophenes, which are likewise a component of the invention, of the formula (V), in which

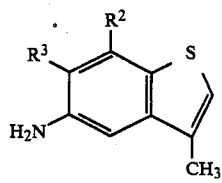
(V)

$R^2$ and $R^3$ have the meaning given in the case of (I), and these are converted into the hydrazine compounds (II) by a known process (compare E. Enders in: Methoden der Organischen Chemie [Methods of Organic Chemistry] (Houben-Weyl), Volume 10, Part 2: Methoden zur Herstellung und Umwandlung von Arylhydrazinen und Arylhydrazonen [Methods of Preparing and Modifying Arylhydrazines and Arylhydrazones], pages 177–406 (1967):

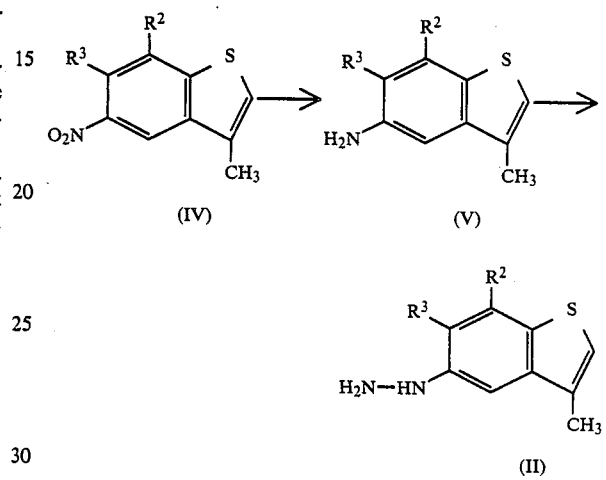

To prepare (V), the nitro compound of the formula (IV) is dissolved in a suitable solvent, such as, for example, methanol, ethanol or ethyl acetate, and is hydrogenated in the presence of a suitable catalyst, such as, for example, palladium, platinum or Raney nickel, under a hydrogen atmosphere at temperatures between 20° C. and 80° C., preferably between 20° C. and 40° C., under normal pressure or increased pressure; or the nitro compound (IV) is dissolved in suitable solvents, for example in alcohols, preferably in methanol or ethanol, excess hydrazine hydrate in a molar ratio of 1:5, preferably in a molar ratio of 1:3, and a hydrogenation catalyst, for example palladium or palladium-on-charcoal, are added and the mixture is heated at 30° C. to 100° C. for 0.5 to 2 hours, preferably at 65° C. to 80° C. for 1 to 2 hours (compare N. B. Chapman et al., J. Chem. Soc. (C), 1968, 518; A. Ricci and N. Cagnoli, Ann. Chim. (Rome), 45, 172 (1955); and C.A. 50, 5564c (1956)).

Working up of the reaction batches to isolate the starting substances (II) and intermediates (IV) for the process according to the invention is carried out in a known manner.

The halogen-substituted 3-methyl-5-nitrobenzothiophene derivatives of the formula (IV) in which $R^2$ and $R^3$ have the meaning given above are new. Their preparation is carried out by methods which are in themselves known, and is shown by way of example in the following equation for the synthesis of 7-fluoro-3-methyl-5-nitrobenzothiophene (IV-1), corresponding to the formula IV in which $R^2$ represents F and $R^3$ represents H:

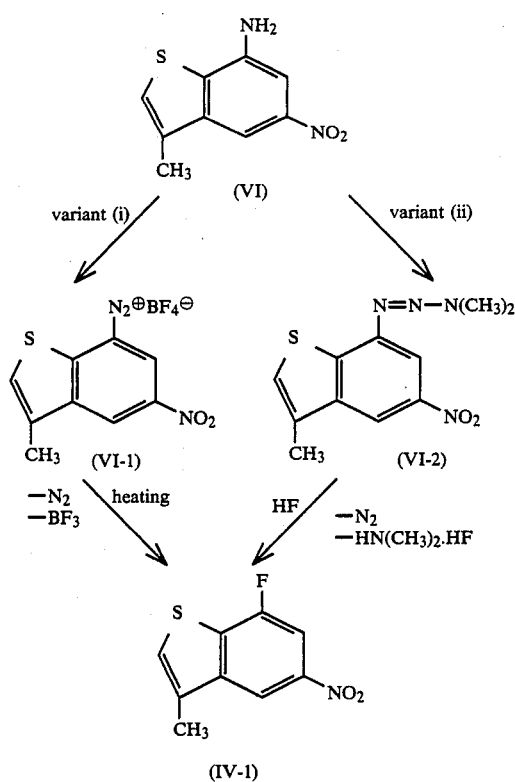

Stage A:

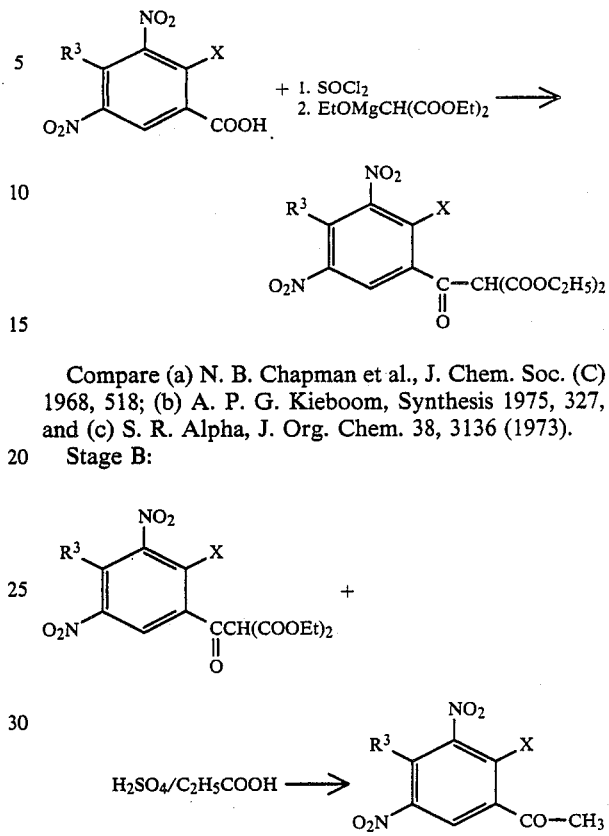

Compare (a) N. B. Chapman et al., J. Chem. Soc. (C) 1968, 518; (b) A. P. G. Kieboom, Synthesis 1975, 327, and (c) S. R. Alpha, J. Org. Chem. 38, 3136 (1973).

Stage B:

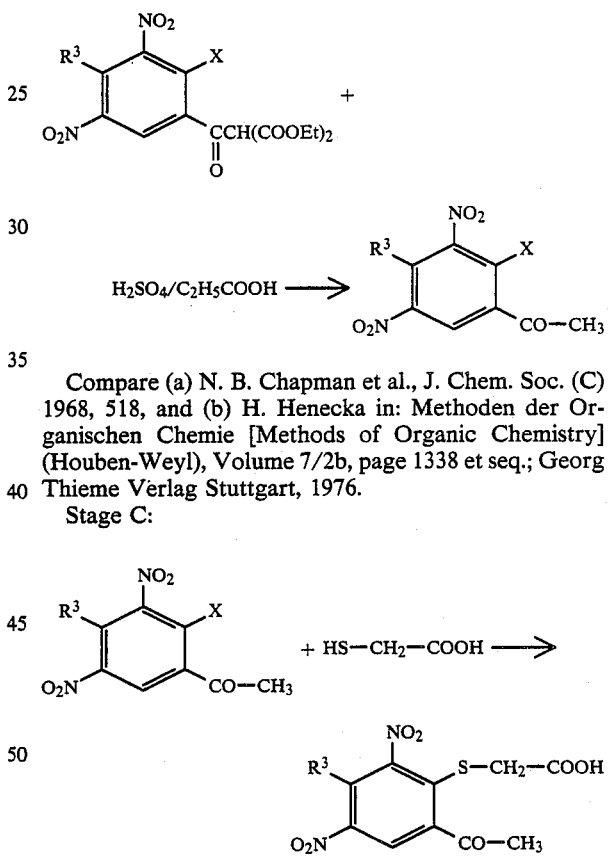

Compare (a) N. B. Chapman et al., J. Chem. Soc. (C) 1968, 518, and (b) H. Henecka in: Methoden der Organischen Chemie [Methods of Organic Chemistry] (Houben-Weyl), Volume 7/2b, page 1338 et seq.; Georg Thieme Verlag Stuttgart, 1976.

Stage C:

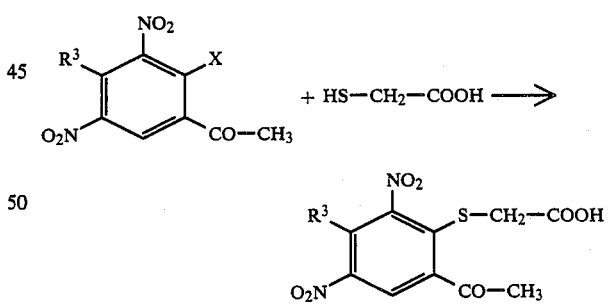

Compare (a) A. Ricci and N. Cagnoli, Ann. Chim. (Rome) 45, 172 (1955); C.A. 50, 5564c (1956); (b) C. Angelini, Ann. Chim. (Rome) 47, 705 (1957); C.A. 52, 1136i (1958); and (c) S. Middleton, Austr. J. Chem. 12, 218 (1959).

Stage D:

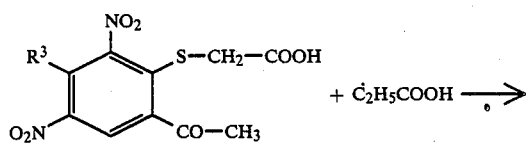

Variant (i) consists of two reaction steps:

1. Diazotisation of the compound (VI) and preparation of the diazonium fluoroborate, for example compound (VI-1). The method, known as the Balz-Schiemann reaction, for the preparation of nuclear-fluorinated aromatic compounds belongs as such to the prior art (compare (a) E. Forche in: Methoden der Organischen Chemie [Methods of Organic Chemistry] (Houben-Weyl), Volume 5/3, pages 213–247; Georg Thieme Verlag Stuttgart, 1962; (b) H. Suschitzky in: Stacy/Tatlow/Sharpe, Advances in Fluorine Chemistry, Volume 4, page 1 et seq.; Butterworths London, 1965; and (c) G. Schiemann and B. Cornils, Chemie und Technologie cyclischer Fluorverbindungen [Chemistry and Technology of Cyclic Fluorine Compounds], pages 9–17, Ferdinand Enke Verlag Stuttgart, 1969).

Variant (ii) is based on the replacement of the triazine group, for example in (VI-2) by a fluorine atom by treating the triazine derivative, which is obtained by diazotisation of (VI) and subsequent reaction of the diazonium compound with secondary amines, preferably dimethylamine (compare E. Müller in: Methoden der Organischen Chemie [Methods of Organic Chemistry] (Houben-Weyl), Volume 10/2, pages 827–835; Georg Thieme Verlag Stuttgart, 1967), with hydrochloric acid, anhydrous hydrogen fluoride or pyridine hydrofluoride (compare (a) M. N. Rosenfeld and D. A. Widdowson, J. Chem. Soc., Chem. Comm. 1979, 914; and (b) G. Schiemann and B. Cornils, Chemie und Technologie cyclischer Fluorverbindungen [Chemistry and Technology of Cyclic Fluorine Compounds], page 8; Ferdinand Enke Verlag Stuttgart, 1969).

The starting compounds (VI) and their intermediates are new. They can be prepared by methods which are in themselves known, for example by the reaction sequence stage A→stage B→stage C→stage D→stage E:

-continued

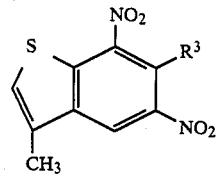

Compare DE-OS [German Published Specification] No. 3,031,738.

Stage E:

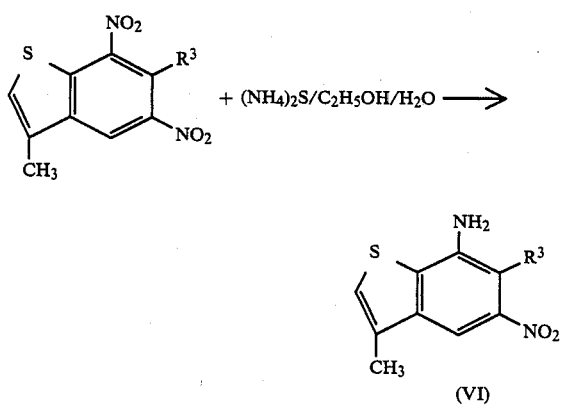

Compare (a) Organ. Synthesis Collect., Volume III, pages 82–84 (1955); and (b) C. Angelini, Ann. Chim. (Rome) 48, 637 (1958); C.A. 53, 5228d (1959).

$R^3$ in the formulae for stages A to E has the meaning given above as preferred. In the formulae for stages A to C, X represents halogen, in particular bromine, chlorine or fluorine, preferably chlorine.

Specific new active compounds which may be mentioned are: 1,9-dimethyl-4-fluoro-7,8,9,10-tetrahydrothieno[3,2-e]pyrido[4,3-b]indole; 1-methyl-9-ethyl-4-fluoro-7,8,9,10-tetrahydrothieno[3,2-e]pyrido[4,3-b]indole; 1,9-dimethyl-5-fluoro-7,8,9,10-tetrahydrothieno[3,2-e]pyrido[4,3-b]indole; 1-methyl-9-ethyl-5-fluoro-7,8,9,10-tetrahydrothieno[3,2-e]pyrido[4,3-b]indole; and 1,9-dimethyl-4,5-difluoro-7,8,9,10-tetrahydrothieno[3,2-e]pyrido[4,3-b]indole.

The present invention includes pharmaceutical formulations which, in addition to non-toxic, inert pharmaceutically suitable excipients, contain one or more compounds according to the invention, or salts thereof, or which consist of one or more compounds according to the invention, or salts thereof, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opalising agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $CC_{14}$-alcohol with $C_{16}$-fatty acid), or mixtures of these substances.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, ground-nut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonide, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the compounds of the formula (I) and/or salts thereof.

The abovementioned pharmaceutical formulations are prepared in the customary manner according to known methods, for example by mixing the active compound or compounds with the excipient or excipients.

The present invention also includes the use of the compounds of the formula (I) and/or salts thereof, and of pharmaceutical formulations which contain one or more compounds of the formula (I) and/or salts thereof, in medicine, for the treatment of the abovementioned diseases.

The active compounds or the pharmaceutical formulations can preferably be administered orally, parenterally and/or rectally, preferably orally and parenterally, and in particular orally and intravenously.

In general, it has proved advantageous in the case of parenteral (intravenous or intramuscular) administration, to administer the active compound or compounds to warm-blooded animals in amounts of about 0.01 to about 10 mg/kg of body weight, preferably 0.1 to 1 mg/kg of body weight, every 24 hours and, in the case of oral administration, to administer them in amounts of about 0.05 to about 100 mg/kg of body weight, preferably 0.1 to 10 mg/kg of body weight, every 24 hours, if necessary in the form of several individual doses, in order to achieve the desired results. An individual dose preferably contains the active compound or compounds in amounts of about 0.01 to about 30 mg/kg of body weight, in particular 0.03 to 3 mg/kg of body weight.

However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

The present invention also relates to medicaments which, besides compounds of the formula (I), also contain other active compounds. Preferred active compounds which may be mentioned are: β-receptor blockers, parasympatholytic agents, anxiolytic agents, neuroleptic agents, hypnotic agents and tranquillisers.

For example 1 the pharmacological activity may be indicated in four test methods relevant for the determination of psychotropic 1. Amphetamine potentiation Substances having an antidepressive action potentiate the stereotype effect induced in rats by amphetamine. The DE$_{50}$ value is the dose of which the amphetamine-induced effect after intravenous administration of 2 mg/kg DL-amphetamine sulphate is increased by 50%.

Lit.: J. L. Howard et al., in Antidepressants: Neurochemical, Behavioral and Clinical Perspectives, herausgegeben von S. J. Enna et al., Raven Press, New York, S. 107-120, 1981

DE$_{50}$ 0,4 mg/kg p.o.

2. Tetrabenazine antagonism

Antidepressants antagonise the ptosis induced in mice by tetrabenazine. The DE$_{50}$ value indicates that dose at which the ptosis induced by tetrabenazine (20 mg/kg p.o.) is reduced by 50%.

Lit.: J. L. Howard et al., Antidepressants: Neurochemical, Behavioral and Clinical Perspectives herausgegeben von S. J. Enna et al., Raven Press, New York, S. 107-120, 1981

DE$_{50}$ 5,5 mg/kg p.o.

3. Anti-aggressive action

Anxiolytics and neuroleptics inhibit aggressive behaviour evoked amongst mice by electric shocks applied to the feet. The DE$_{50}$ value is the dose at which the aggressive behaviour is reduced by 50%.

Lit.: Tedeschi et al., J. Pharmacol. Exp. Ther. 129: 28-34, 1954.

DE$_{50}$ 7,7 mg/kg i.p.

4. Avoidance behaviour

Rats avoid entering a dark box in which they had previously been given an electric shock applied to the feet. This avoidance behaviour is eliminated on administering anxiolytics. The lowest effective dose at which the avoidance behaviour is significantly reduced is indicated.

Lit.: Ader et al., Psychon. Sci. 26: 125-128, 1972.

Lowest effective dose: 2,5 mg/kg i.p.

The present invention may be illustrated in more detail by the following examples.

EXAMPLE 1

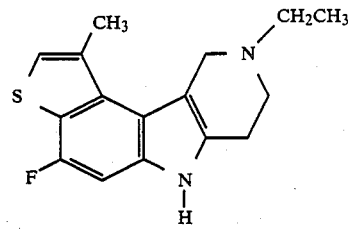

1-Methyl-9-ethyl-4-fluoro-7,8,9,10-tetrahydro-thieno[3,2-e]pyrido[4,3-b]indole 0.1 mole of 3-methyl-7-fluoro-5-hydrazinobenzothiophene hydrochloride and 0.11 mole of 1-ethylpiperidone are dissolved in 300 ml of isopropanol in the cold. The solution is brought to the boiling point and 100 ml of isopropanol saturated with HCl is added in the course of 10 minutes, under the influence of heat. After the mixture has been boiled for 1 hour, it is cooled to 0° C. and the crystals formed are filtered off with suction. For purification, 300 ml of 10% strength sodium hydroxide solution are added to the crude product, the base is taken up in methylene chloride and, after washing with water, the organic phase is dried over sodium sulphate. After filtration and evaporation of the solvent, the base is obtained as crystals from isopropyl ether.

Yield: 75% of theory; melting point: 182°-183° C., after recrystallisation from ethyl acetate.

Lactate: 0.05 mole of the base is dissolved in 700 ml of acetone, and 15 g of L(+)-lactic acid are added. Colourless crystals. Yield: 95% of theory; melting point: 203°-205° C.

The following compound is prepared analogously: 1,9-dimethyl-4-fluoro-7,8,9,10-tetrahydrothieno[3,2-e]pyrido[4,3-b]indole.

Yield: 45% of theory; melting point 234°–235° C., after recrystallisation from ethyl acetate.

Preparation of the starting substances

3-Methyl-7-fluoro-5-hydrazinobenzothiophene hydrochloride

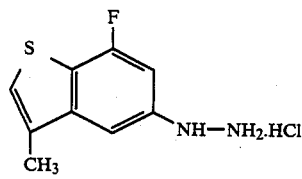

0.1 mole of 3-methyl-7-fluoro-5-aminobenzothiophene hydrochloride is suspended in 100 ml of water and 100 ml of concentrated hydrochloric acid, and a solution of 0.11 mole of sodium nitrite in 50 ml of water is added dropwise at between −5° C. and 0° C. The diazonium salt solution is added dropwise to a mixture, cooled to 0° C., of 0.21 mole of $SnCl_2.2H_2O$ and 200 ml of concentrated hydrochloric acid. After the mixture has been warmed to room temperature, 60 ml of isopropanol are added and the crystal mass is filtered off with suction and recrystallised from isopropanol.

Yield: 88% of theory; melting point: 205°–210° C. (decomposition).

3-Methyl-7-fluoro-5-aminobenzothiophene hydrochloride

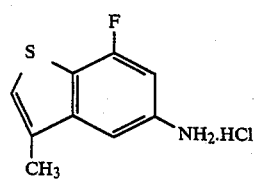

Process a 0.01 mole of 3-methyl-7-fluoro-5-nitrobenzothiophene is hydrogenated in 300 ml of methanol in the presence of 1 g of palladium-on-charcoal at 25° C. After the catalyst has been filtered off, the filtrate is concentrated to about 100 ml, an ether/HCl solution is added and the hydrochloride is filtered off with suction.

Yield: 92% of theory; melting point: 273°–275° C. (decomposition).

Process b 0.09 mole of 3-methyl-7-fluoro-5-nitrobenzothiophene is heated to the boiling point in 220 ml of methanol together with 2 g of palladium-on-charcoal. 0.35 mole of hydrazine hydrate is then added dropwise in the course of 30 minutes. After the mixture has been boiled for 2 hours, it is filtered, the filtrate is concentrated, the residue is dissolved in ether and the solution is washed with water. The hydrochloride is precipitated from the ether solution.

Yield: 97% of theory; melting point: 273°–275° C. (decomposition).

3-Methyl-7-fluoro-5-nitrobenzothiophene

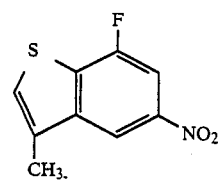

0.5 mole of 1,1-dimethyl-3-(3-methyl-5-nitrobenzothiophen-7-yl)-triazene is introduced in portions into 10 moles of hydrofluoric acid. The apparatus is then closed, 5 bar of nitrogen are forced in and the mixture is warmed to 100° C. The nitrogen formed is let down continuously under 9 bar. When the reaction had ended (about 1 hour), the mixture is cooled to room temperature, the residual pressure is let down and excess HF is distilled off in vacuo. The residue is stirred in methylene chloride and the mixture is washed neutral with water and finally with $NaHCO_3$ solution, dried and concentrated. The product is purified by recrystallisation from light petroleum.

Yield: 60% of theory; melting point: 109°–110° C.

1,1-Dimethyl-3-(3-methyl-5-nitrobenzothiophen-7-yl)-triazene

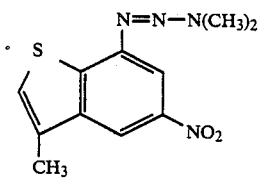

0.05 mole of 3-methyl-5-nitro-7-aminobenzothiophene is dissolved in 100 ml of concentrated sulphuric acid, while cooling with ice, and is diazotised at 10° C. by dropwise addition of 0.05 mole of nitrosylsulphuric acid. After 15 minutes, the mixture is poured onto 700 g of ice, 0.06 mole of dimethylamine (40% strength aqueous dimethylamine solution) is added and the mixture is rendered alkaline with 20% strength sodium hydroxide solution. The triazene is then extracted by shaking with methylene chloride and the organic solution is washed with water and dried over $Na_2SO_4$. The crystalline residue obtained after filtration and evaporation of the solvent is taken up in a little methylene chloride and chromatographed on $Al_2O_3$ (eluting agent: methylene chloride/cyclohexane (1:1)). The product obtained after evaporation of the eluate is recrystallised from isopropanol.

Yield: 63% of theory; melting point: 147°–148° C.

3-Methyl-5-nitro-7-aminobenzothiophene

Stage E

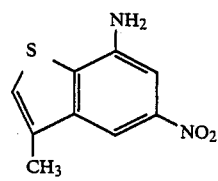

453 ml of a 20% strength ammonium sulphide solution (1.33 moles of $(NH_4)_2S$) are added dropwise to a suspension of 0.4 mole of 3-methyl-5,7-dinitrobenzothiophene in 1,400 ml of ethanol at 55°–60° C. in the course of 45 minutes, and the mixture is then heated at the boiling point for 15 minutes. The mixture is then diluted with 1,400 ml of water and cooled to 0° C. and the crystalline product is filtered off with suction. For purification, the crystals are dissolved in methylene chloride and the solution is filtered over a silica gel column (eluting agent: methylene chloride/cyclohexane 9:11). The substance obtained from the combined eluates is recrystallised from isopropanol.

Yield: 79% of theory; melting point: 147°–148° C.

3-Methyl-5,7-dinitrobenzothiophene

Stage D

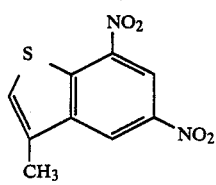

A solution of 0.8 mole of (2-acetyl-4,6-dinitrophenylthio)acetic acid in 1 liter of propionic acid is heated at the boiling point until the evolution of $CO_2$ has ended (about 4 hours).

The propionic acid is then distilled off, the crystalline residue is taken up in methylene chloride and the solution is filtered over an $Al_2O_3$ layer. The product obtained after concentration of the filtrate is boiled up in isopropanol, filtered off and dried.

Yield: 68% of theory; melting point 174°–175° C.

(2-Acetyl-4,6-dinitrophenylthio)acetic acid

Stage C

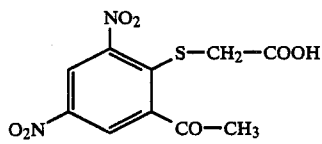

0.85 mole of 2-chloro-3,5-dinitroacetophenone and 1.7 moles of sodium bicarbonate are suspended in a mixture of 650 ml of isopropanol and 250 ml of water. 0.95 mole of mercaptoacetic acid is added dropwise in the course of 10 minutes and the mixture is stirred at 25° C. for 2 hours and finally at 45° C. for 30 minutes. 1.8 liters of ice-water and 140 ml of concentrated hydrochloric acid are then added and the crystals are filtered off with suction. The dried product is recrystallised from isopropanol.

Yield: 95% of theory; melting point 136°–137° C.

2-Chloro-3,5-dinitroacetophenone

Stage B

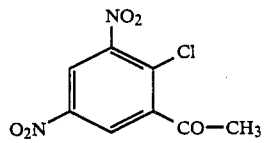

After addition of 6 ml of concentrated sulphuric acid, a solution of 1.1 moles of diethyl (2-chloro-3,5-dinitrobenzoyl)-malonate in 500 ml of propionic acid is heated at the boiling point for 3 hours. The propionic acid is then distilled off and 1.5 liters of ice-water are added to the residue. The crystalline reaction product is filtered off with suction, washed with water and dried. The product is dissolved in methylene chloride and the solution is filtered over a 6 cm thick layer of $Al_2O_3$. After addition of 1 liter of isopropanol, the filtrate is concentrated and the crystals which separate out are filtered off with suction and dried.

Yield: 74% of theory; melting point: 109°–110° C.

Diethyl (2-chloro-3,5-dinitrobenzoyl)-malonate

Stage A

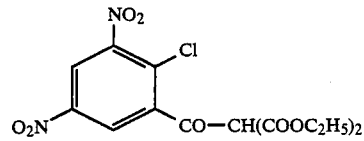

A solution of 1.14 moles of 2-chloro-4,5-dinitrobenzoyl chloride (prepared from 2-chloro-3,5-dinitrobenzoic acid by boiling in $SOCl_2$ for 20 hours) in 1.8 liters of absolute toluene is added dropwise to a solution of 1.7 moles of diethyl ethoxymagnesium-malonate in 550 ml of absolute toluene at room temperature, the mixture is subsequently stirred for 30 minutes and 1 kg of ice and 150 ml of 2N sulphuric acid are then added. The organic phase is separated off, washed neutral with water and concentrated. Crystallisation takes place after addition of 2 liters of petroleum ether (boiling range: 40°–60° C.).

Yield: 95% of theory; melting point: 71°–72° C.

What is claimed is:

1. A 7,8,9,10-tetrahydrothieno[3,2-e]pyrido[4,3-b]-indole of the formula

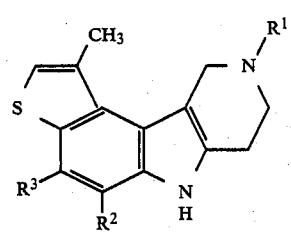

in which $R^1$ represents hydrogen or straight-chain or branched alkyl with 1 to 4 C atoms and $R^2$ and $R^3$ represent fluorine or hydrogen wherein at least one of $R^2$ or $R^3$ is fluorine and an acid addition salt thereof.

2. A compound of the formula I according to claim 1, in which $R^1$ represents methyl or ethyl, $R^2$ represents fluorine and
$R^3$ represents hydrogen.

3. A pharmaceutical composition containing as an active ingredient an antidepressant effective amount of a compound of claim 1 in admixture with an inert pharmaceutical carrier.

4. A pharmaceutical composition containing as an active ingredient an antidepressant effective amount of a compound of claim 1 in the form of a sterile or physiologically isotonic aqueous solution.

5. A composition of claim 3 containing from 0.5 to 90% by weight of the said active ingredient.

6. A medicament in dosage unit form comprising an antidepressant effective amount of a compound of claim 1 and an inert pharmaceutical carrier.

7. A medicament of claim 6 in the form of tablets, pills, dragees, capsules, ampoules or suppositories.

8. A method of combatting depression in warm-blooded animals which comprises administering to said animals an antidepressant effective amount of an active compound of claim 1 either alone, in admixture with a diluent or in the form of a medicament.

9. A method according to claim 8 in which the active compound is administered in an amount of about 0.05 to about 100 mg/kg of body weight per day.

10. A method of claim 9 in which the active compound is administered in an amount of about 0.1 to about 10 mg/kg of body weight per day.

11. A compound of claim 1 which is 1,9-dimethyl-4-fluoro-7,8,9,10-tetrahydrothieno[3,2-e]pyrido[4,3-b]indole.

12. A compound of claim 1 which is 1-methyl-9-ethyl-4-fluoro-7,8,9,10-tetrahydrothieno[3,2-e]pyrido[4,3-b]indole.

13. A compound of claim 1 which is 1,9-dimethyl-5-fluoro-7,8,9,10-tetrahydrothieno[3,2-e]pyrido[4,3-b]indole.

14. A compound of claim 1 which is 1-methyl-9-ethyl-5-fluoro-7,8,9,10-tetrahydrothieno[3,2-e]pyrido[4,3-b]indole.

15. A compound of claim 1 which is 1,9-dimethyl-4,5-difluoro-7,8,9,10-tetrahydrothieno[3,2-e]pyrido[4,3-b]indole.

* * * * *